United States Patent
Van Der Mark et al.

(10) Patent No.: US 10,267,999 B2
(45) Date of Patent: Apr. 23, 2019

(54) OPTICAL CONNECTOR FOR STERILE APPLICATIONS

(71) Applicant: KONINKLIJKE PHILIPS N.V., Eindhoven (NL)

(72) Inventors: Martinus Bernardus Van Der Mark, Best (NL); Eibert Gerjan Van Putten, 's-Hertogenbosch (NL); Hendrina Helena Aleida Evenaar-Geven, Ysselsteyn (NL); Godefridus Johannes Verhoeckx, Eindhoven (NL); Adrianus Wilhelmus Dionisius Maria Van Den Bijgaart, Helvoirt (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/125,998

(22) PCT Filed: Mar. 24, 2015

(86) PCT No.: PCT/EP2015/056165
§ 371 (c)(1),
(2) Date: Sep. 14, 2016

(87) PCT Pub. No.: WO2015/150149
PCT Pub. Date: Oct. 8, 2015

(65) Prior Publication Data
US 2017/0082806 A1 Mar. 23, 2017

(30) Foreign Application Priority Data
Mar. 31, 2014 (EP) ..................................... 14162660

(51) Int. Cl.
*G02B 6/36* (2006.01)
*G02B 6/38* (2006.01)
(Continued)

(52) U.S. Cl.
CPC .......... *G02B 6/3866* (2013.01); *A61B 5/0084* (2013.01); *G02B 6/387* (2013.01);
(Continued)

(58) Field of Classification Search
USPC ...................................................... 385/30, 68
See application file for complete search history.

(56) References Cited

U.S. PATENT DOCUMENTS 5,434,941 A * 7/1995 Bechtel .................. G02B 6/421
                                                         385/68
5,815,619 A * 9/1998 Bloom ................. G02B 6/3855
                                                         385/60
(Continued)

FOREIGN PATENT DOCUMENTS

CN     101535858 A     9/2009

OTHER PUBLICATIONS

Marcuse, D., "Loss analysis of single-mode fiber splices", The Bell System Technical Journal, vol. 56, No. 5, May-Jun. 1977, pp. 703-718.

*Primary Examiner* — Eric Wong

(57) ABSTRACT

An optical connector system for reversible optical connection between two optical fibers (102, 104) with their end parts inside respective ferrules. A receptacle arrangement has a receiving body (105) for receiving at least one of the ferrules (103). An optical element (106) of the receptacle arrangement serves to provide optical connection between the two optical fibers in a connected state of the optical connector system, and at the same time, the optical element (106) serves as a sterility barrier between the two optical fibers. The optical element (106) can be an optical waveguide, e.g. a piece of optical fiber similar to the two optical fibers (102, 104), and arranged within the receiving body (105). Alternatively, the optical element may be a thin flexible membrane (207, 307) which is optically transparent.

(Continued)

As a further alternative, the optical element may be a sterilizing fluid (409) arranged inside a container that can be punctured upon insertion of one of the ferrules (401, 403) into the container (408), to allow an optical fiber end to be sterilized by the fluid (409) prior to entering into the connected state. In a further embodiment, an optical lens (312) is used to project light from one fiber end through a membrane (307) to the opposite fiber end.

14 Claims, 2 Drawing Sheets

(51) Int. Cl.
    *A61B 5/00*         (2006.01)
    *A61B 90/30*       (2016.01)

(52) U.S. Cl.
    CPC ......... *G02B 6/3825* (2013.01); *G02B 6/3853* (2013.01); *G02B 6/3871* (2013.01); *G02B 6/3885* (2013.01); *A61B 2090/306* (2016.02); *A61B 2562/228* (2013.01)

(56) References Cited

U.S. PATENT DOCUMENTS

| | | | |
|---|---|---|---|
| 5,949,929 A * | 9/1999 | Hamm | A61B 18/24 |
| | | | 385/25 |
| 7,422,375 B2 * | 9/2008 | Suzuki | G02B 6/255 |
| | | | 385/53 |
| 2008/0019642 A1 | 1/2008 | Kewitsch | |

* cited by examiner

OPTICAL CONNECTOR FOR STERILE APPLICATIONS

CROSS-REFERENCE TO PRIOR APPLICATIONS

This application is the U.S. National Phase application under 35 U.S.C. § 371 of International Application Serial No. PCT/EP2015/056165, filed on Mar. 24, 2015, which claims the benefit of European Patent Application Serial No. 14162660.6, filed on Mar. 31, 2014. These applications are hereby incorporated by reference herein.

FIELD OF THE INVENTION

The present invention relates to the field of connectors for optical fibers. More specifically, this invention relates to optical connections allowing connection and disconnection in a sterile zone.

BACKGROUND OF THE INVENTION

In minimally invasive medical interventions needles, guide wires, sheaths and catheters are inserted in the patient in order to find and measure, on the one hand, the relevant anatomy of the patient and treat or place a stent (for example) on the other hand. Clearly, the part of the devices inserted into the patient either must be sterile at all times or should only be contaminated with fluids and tissue from the patient itself. When a needle, guide wire or catheter is armed with a sensor or actuator, some connection (for example electrical wire or optical fiber) must be made to transmit the information or power to or from a controller or interrogator placed in the non-sterile zone, away from the patient. Somewhere along the transmission line, the sterile zone meets the non-sterile zone. This setup requires proper management of sterility.

The use of optical interrogation techniques in minimally invasive medical interventions requires that, on the one hand, the optical sensor is inserted in the patient and must be sterile and, on the other hand, that the optical waveguide that transmits the optical information is plugged into a mating sleeve of a patch cord, controller or interrogator placed in the non-sterile zone, away from the patient. Upon making the optical connection, the sterile proximal end of the optical sensor comes in contact with the non-sterile patch cord, controller or interrogator thereby also becoming non-sterile. During a medical procedure a sterility problem may arise in case the optical waveguide needs to be disconnected and the (now non-sterile) proximal end of the medical device containing the optical sensor needs to enter the sterile zone or when devices have to slide over the medical device containing the optical sensor. The latter is for example the case when a so-called back-loadable guide wire armed with optical shape sensing (OSS) is used. In essence, whenever the proximal end of a guide wire becomes non-sterile, the next device (a catheter or stent) that slides over it will transport the contamination into the body of the patient.

U.S. Pat. No. 5,949,929 discloses an interventional medical device having a rotatable optical fiber, an assembly having a conduit for conveying a light beam to the rotatable fiber as well as a rotor and a fixed housing, and a coupling. The coupling includes a rotatable portion attachable to a proximal end of the rotatable fiber and to the rotor so as to permit the rotatable fiber to rotate continuously with the rotor while the rotatable fiber remains in axial alignment with the light beam. The proximal end of the rotatable portion of the coupling has a V-shaped coupling surface that complements a distal end surface of the rotor. In some embodiments, a GRIN (gradient index of refraction) lens is arranged between the stationary optical fiber and the rotatable optical fiber which reduces the need for precise alignment of the optical fibers.

SUMMARY OF THE INVENTION

It would be advantageous to provide an optical connector system that is non-sterile at one end, but remains sterile at the other end. E.g. to allow medical back-loading procedures, e.g. so as to allow optical shape sensing to be applied in medical back-loading procedures. Further, it would be advantageous that the optical connector provides a high insensitivity to rotation, thus allowing application for rotation sensitive optical fibers. Still further, the connector system should be possible to manufacture in miniature versions.

In a first aspect, the invention provides an optical connector system arranged to provide a reversible optical connection between associated first and second optical fibers, comprising:
  a first ferrule with an outer body and arranged for having an end portion of the associated first optical fiber arranged inside,
  a second ferrule with an outer body and arranged for having an end portion of the associated second optical fiber arranged inside, and
  a receptacle arrangement comprising a receiving body, wherein the receptacle arrangement is arranged to receive an end part of the outer body of at least the second ferrule, wherein the receptacle arrangement further comprises an optical element serving to provide optical connection between the associated first and second optical fibers in a connected state of the optical connector system, and wherein the optical element serves as a sterility barrier between the associated first and second optical fibers.

Such optical connector system is advantageous since it allows e.g. the first ferrule to be non-sterile, while the second ferrule is sterile, since the optical element serves as a sterility barrier, e.g. for connecting a sterile guidewire and a non-sterile patch cord. Still, the connector system can be manufactured in versions that allows medical back-loading procedures. The optical connector system is further advantageous since it is well suited for miniature applications, due to the low complexity and the possibility of implementation with few single components.

E.g. the optical connector system may be used to connect a guidewire that may be used for optical tissue examination and/or optical shape sensing (OSS). The first and second optical fibers may be single or multi-core optical fibers. It is to be understood that the optical element serves to provide optical connection between the first and second optical fibers. Preferably, the optical element, e.g. an optical waveguide, is selected to match the type of the first and second optical fibers, so as to provide a low optical low loss in the connected state, and so as to provide optical connection, in the connected state, between each single fiber core of the first and second optical fibers, in case these comprise multiple fiber cores.

Furthermore it is advantageous to make the connector system allow for rotational alignment of the first and second optical fibers. A not limited list of examples of optical fibers where such a connector system is advantageous are: 1) optical fibers with off-axis core(s), such as multi-core fibers, 2) photonic crystal fibers which do not have a circular symmetric core-structure, 3) optical fibers where the core has different polarization dependent propagation properties, such as in polarization maintaining fibers, and 4) optical fibers with an angle polished end facet, as is typical for angled physical contact (APC) connections.

By 'ferrule' is understood an element serving to at least partly encapsule the end of the optical fiber. Thus, e.g. a guide-wire or similar is understood to be a ferrule. The ferrule may in general be formed by various materials, e.g. polymers, metals or combinations thereof.

In the following, a number of embodiments or optional features will be defined.

The receptacle arrangement may be arranged to receive the end part of the outer body of the first ferrule in one end, and to receive an end part of the outer body of the second ferrule in its opposite end, and wherein the optical element comprises an optical waveguide arranged within the receiving body. Especially, the optical waveguide may be similar to the first and second optical fibers, e.g. formed by the same material as one of or both of the first and second optical fibers or at least have similar optical interfaces. The waveguide may be formed integrally with the receiving body, e.g. positioned inside the receiving body and fastened to the receiving body. The optical waveguide serves as a sterility barrier, since it can be sterile in one end while non-sterile in its opposite end.

The optical element may comprise an optically transparent membrane. Especially, the optically transparent membrane may be flexible, i.e. it may be formed by a flexible, and arranged to partially encapsulate the associated first or second optical fiber (or at least partially encapsulate the first or second ferrule) in the connected state. The optical connector system may further comprise a plug arranged to receive the first ferrule, and wherein the plug is arranged to fit inside the receiving body. Especially, the plug may be arranged to receive the first ferrule in one end, and wherein the optically transparent membrane is positioned at an opposite end of the plug. Especially, the optical connector system may comprise a first plug arranged to receive the first ferrule, wherein the first plug is arranged to fit inside a second plug, and wherein the second plug is shaped to fit inside the receiving body. E.g. the optically transparent membrane is positioned to cover one end of the second plug.

The sterility barrier may strongly absorb or strongly reflect light at a wavelength different than the usual operation wavelength (where it should be highly transparent). Strong absorption can be delivered by a dye while strong reflection can be achieved by writing a fiber Bragg grating into the barrier with the proper periodicity. By sending a pulse of light with a wavelength in the absorption/reflection band and by detecting how much of the pulse is being reflected one can detect if the sterility barrier is present in the optical path or not.

The optical connector system may comprise a second optical element arranged to project light from one of the associated first and second optical fibers via the optically transparent membrane to the opposite one of the associated first and second optical fiber. Especially, the second optical element may comprise an optical lens, or a combination of optical lenses, or mirrors, positioned between the first optical fiber and the optically transparent membrane. Such embodiments allows optical connection without any structural contact between the receptable arrangement and the first ferrule.

The receptable arrangement may comprise a container with a sterilizing fluid. Said container may be arranged to receive the first ferrule and be arranged to puncture upon insertion of the first ferrule into the container, so as to allow sterilization of at least an end part of the associated first optical fiber by means of contact with the sterilizing fluid, upon insertion of the first ferrule insertion into the container. The container may be formed as a (replacable) cartridge. Especially, a sponge element may be comprised within the container, wherein at least a part of said sterilizing fluid is soaked into the sponge element. The sponge element may be arranged to mechanically clean at least part of the associated first optical fiber during insertion of the first ferrule into the container, prior to entering into the connected state. More specifically, the sponge element may have a prefabricated hole arranged for the first ferrule to penetrate through, so as to allow the associated first optical fiber to provide optical connection with the associated second optical fiber, in the connected state.

It may be preferred that the receiving body is arranged to surround end parts of outer bodies of both of the first and second ferrules in a connected state of the optical connector system. Hereby, the connection between the first and second ferrules can be encapsulated or at least shielded.

The first and second ferrules may have outer bodies with non-circular cross sections of at least their end parts, and wherein the receptacle arrangement forms a receiving opening arranged to receive the end parts of the outer bodies of the first and second ferrules from opposite sides, and wherein a cross-sectional shape of a receiving opening at least partly matches the non-circular shape of the end parts of the outer bodies of the first and second ferrules, so as to provide a rotational locking mechanism serving to restrict relative rotation between the first and second ferrules. Such embodiment provides a high rotational stablility, and is thus especially suited for first and second optical fibers with multile fiber core. By 'non-circular cross section of at least an end part' is to be understood an end part which does not have a circular cross section around its entire periphery. Such total circular cross section would not be able to provide the advantageous rotational locking or inhibiting effect of the first and second ferrules by engagement with the receptacle arrangement. However, the cross section of the end part of the first and second ferrules may be partly circular, i.e. circular along a part of its periphery, while non-circular, e.g. flat, on the remaining part of its periphery.

The associated first and second optical fibers may be mounted rotationally fixed to the respective first and second ferrule, so as to ensure that the first and second optical fibers are effectively rotationally locked by the optical connector system.

The receiving opening may have different cross-sectional shapes in each end, being shaped to fit respective first and second ferrule outer bodies with different cross-sectional shapes. In other embodiments the first and second ferrules have similar outer body cross-sectional shapes, thus being shaped to fit a receiving opening with similar cross-sectional shape in both ends.

The system may comprise a separate element serving to fix or lock the first and second ferrules together in a longitudinal direction, so as to provide a stable optical connection between the first and second optical fibers. Such separate element may be a polymeric element, a metallic element, or the longitudinal fixing or locking it may be provided by a shrink tube around the first and second ferrules.

Preferably, the optical connector system is arranged for reversibly connection such that a user can connect and disconnect the first and second optical fibers by means of the optical connection system, without the need for any tool.

The first and second associated optical fibers may be multi-core optical fibers. An example of a specific type of multi-core optical fiber is an optical fiber comprising four single mode optical fiber cores, e.g. one central fiber core, and three additional fiber cores helically arranged around the central fiber core.

In a second aspect, the invention provides an optical system comprising first and second optical fibers, and an optical connector system according to the first aspect.

In a third aspect, the invention provides a medical system comprising an interventional medical device optically connected to an optical system according to the second aspect.

In a fourth aspect, the invention provides a method for reversibly connecting first and second optical fibers, the method comprising:

providing a first ferrule with an outer body and an end portion of the first optical fiber arranged inside, providing a second ferrule with an outer body and an end portion of the second optical fiber arranged inside, and providing a receptacle arrangement with an optical element, and inserting at least an end part of the outer body of the first ferrule into a receptacle arrangement comprising an optical element, so as to provide optical connection between the first and second optical fibers via the optical element, wherein the optical element serves as a sterility barrier between the first and second optical fibers.

It is appreciated that the same advantages and embodiments of the first aspect apply as well for the second, third, and fourth aspects. In general the first, second, third, and fourth aspects may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
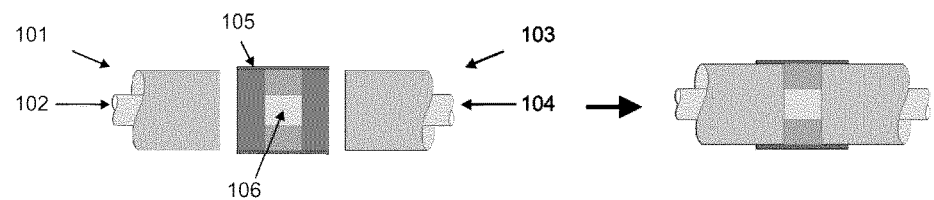
FIG. 1 shows a sketch of an embodiment with an optical waveguide acting as sterility barrier.

FIG. 1 illustrates a side section view of an optical connector system embodiment where a receptacle arrangement forms a connecting piece 105, 106 for connecting two ferrules 101, 103. To the left a sketch shows the system in a disconnected state, and to the right the system is shown in a connected state. First and second ferrules 101, 103 have respective first and second optical fibers 102, 104 arranged therein. The optical fibers 102, 104 may be multi-core optical fibers, and they reside in the center of the ferrules 101, 103. Ends of the ferrules 101, 103 are inserted from opposite ends of a receiving body 105 forming part of a receptacle arrangement. An optical element 106 in the form of a short optical waveguide, e.g. multi-core waveguide, is arranged inside the receiving body 105. The optical element 106 serves to provide an optical connection between the first and second optical fibers 102, 104 in a connected state, namely by forming an optical transmission path, or multiple transmission paths, between the end of the first optical fiber 102 and the end of the second optical fiber 104, in the connected state. The optical element 106 may be mounted in a fixed manner inside the receiving body 105, and the optical element 106 serves as a sterility barrier between the first and second optical fibers 102, 104, since it prevents the first and second optical fibers 102, 104 from entering into contact. Thus, the second optical fiber 104 and the second ferrule 103 may continue to be sterile even after optical connection to the first optical fiber 102, and the first ferrule 101 which are non-sterile.

For a low loss optical connection, it is required to have the mode structure and the geometry of the sterility barrier waveguide 106 as similar as possible to the optical fibers 102, 104 to be connected. The fact that the optical element 106 forming the optical connection is a waveguide or optical fiber itself ensures that the optical mode does not diverge on propagating from the non-sterile optial fiber 102 to the sterile optical fiber 104. Especially in case the first and second optical fibers 102, 104 are multi-core optical fibers, a rotational locking arrangement may be provided so as to prevent relative rotation between the first and second ferrules 101, 103, and the optical element 106.

The optical element 106 may be made sterilizable such that it can be re-used for multiple medical interventions. Preferably, the optical element 106 may be made an integral part of the receiving body 105, that forms a hermetic seal and is sterilized with the receiving body 105.

Figure 2:
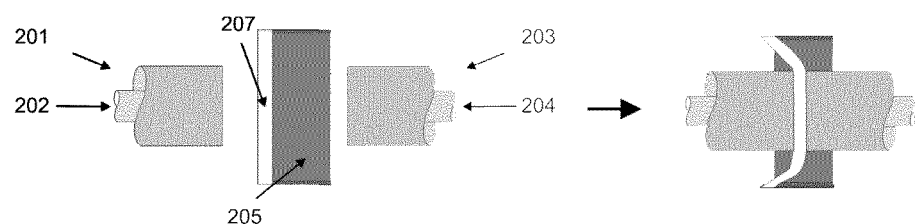
FIG. 2 shows a sketch of an embodiment with a thin flexible membrane acting as sterility barrier.

FIG. 2 shows a side section view of an embodiment with an optical element in the form of a thin membrane 207 positioned between the two optical fibers 202, 204 to act as a sterility barrier. To the left the embodiment is shown in a disconnected state, i.e. with the ferrules 201, 203 outside the receiving body 205. The thin and flexible membrane 207 covers one end of the receiving body 205. To the right, the connected state is shown, where the ferrules 201, 203 have been inserted into the receiving body 205 from opposite sides, and where the flexible membrane 207 now partly encapsulates the first ferrule 201, and the membrane 207 serves to prevent direct contact between the first and second optical fibers 202, 204.

The membrane 207 could be either sterilizable or sterile and disposable after each intervention. The membrane 207 is preferably optically sufficiently transparent, at least for the intended wavelength range, to allow light to couple from the first optical fiber 202 to the second optical fiber 204 through the membrane 207. In contrast to the embodiment in FIG. 1, the membrane 207 itself does not guide the light in a finite area. The optical mode coming from one optical fiber 202 will just diverge as it propagates through the membrane 207. It will therefore induce some coupling loss at the other optical fiber 204, depending on the thickness of the membrane 207. Assuming that both optical fibers 202, 204 have the same propagating mode (or propagating modes in e.g. a multicore fiber) with a radius $w_0$, the power transmission T as function of a gap distance $\Delta z$ introduced by the membrane is given by $$T = \frac{1}{1 + \left[\frac{\Delta z \lambda}{2\pi n w_0^2}\right]^2},$$

where n is the refractive index of the membrane and λ the wavelength of the light. See e.g. "*Loss Analysis of Single-Mode Fiber Splices*", D. Marcuse, *The Bell System Technical Journal, Vol.* 56, *No.* 5, *May-June* 1977, *pp.* 703-718. For realistic parameters it means that if we want to keep the insertion loss lower or equal to 1 dB, the membrane thickness is preferably in the order of a few tens of micrometers or thinner.

Further, in order to minimize the reflections at the interface between the membrane 207 and the optical fibers 202, 204, the refractive index of the membrane 207 is preferably selected to be as close as possible to that of the optical fibers 202, 204.

A possible suitable material for the membrane 207 is fluorinated polymers to keep both the refractive index low and contamination low. Further suitable materials are polyimide (thin and strong), polyethylene (stretchable), high-density polyethylene (HDPE), Para film (stretchable), latex (stretchable).

In an alternative version of the embodiment of FIG. 2, the membrane 207 is either very plastic or elastic, or it may have a tubular or conical shape, so that it fits around an end of one of the ferrules 201, 203.

Figure 3:
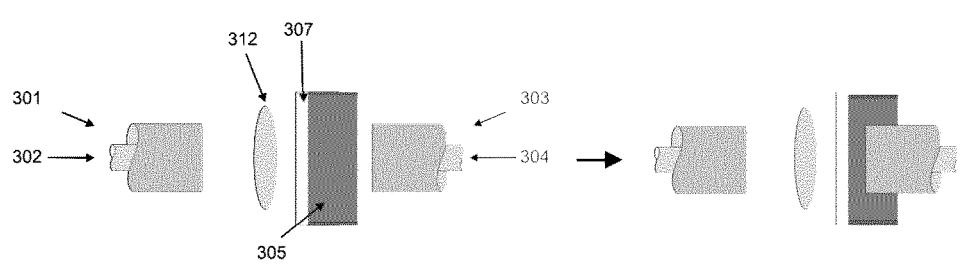
FIG. 3 shows a sketch of an embodiment with a combination of a membrane and an optical lens.

FIG. 3 shows side view sketches of an embodiment for connecting first and second ferrules 301, 303, with respective optical fibers 302, 304 arranged inside. Again, the sketch to the left shows a disconnected state, while the connected state is shown to the right. A thin optically transparent membrane 307 is arranged to cover one end of a receiving body 305 which is arranged to receive the second ferrule 303 from the opposite end. Apart from the membrane 307, the receptable arrangement comprises a further optical element (or multiple optical elements), namely an optical lens 312 positioned between the first and second optical fiber 302, 304, e.g. acting as a relay lens. Here, it is shown positioned between the first optical fiber 302 and the membrane 307. This arrangement does not require that the two optical fibers 302, 304 are as close as possible, but the optical element(s) 312 can project one optical interface onto the other allowing for more design freedom of the transparent membrane 307. The optical element(s) 312 are preferably placed at the side of the non-sterile optical fiber 302 so that it does not have to be sterile or sterilized.

Figure 4:
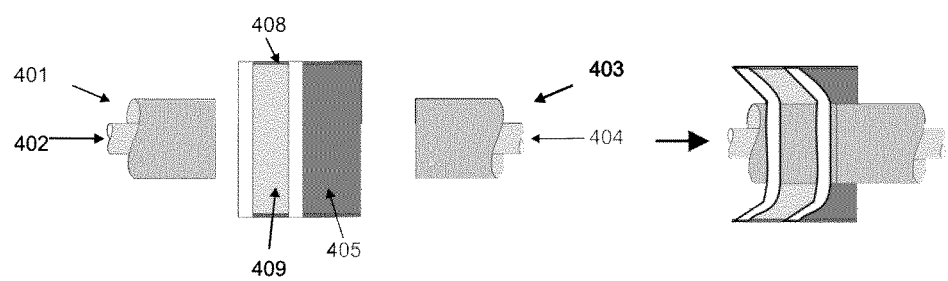
FIG. 4 shows a sketch of an embodiment with a cartridge containing a sterilizing fluid.

FIG. 4 shows side view sketches of an embodiment for connecting first and second ferrules 401, 403, with respective optical fibers 402, 404 arranged inside. Again, the sketch to the left shows a disconnected state, while the connected state is shown to the right. This embodiment comprises a container 408, e.g. formed as a cartridge, with sterilizing fluid 409, such as alcohol or some iodine solution, to sterilize the non-sterile optical fiber 402 right before the actual connection to the second optical fiber 404 is made. The sterilization could be done by having a cartridge 408 with sterilizing fluid 409 or gas that will be punctured upon insertion of the non-sterile part, i.e. the first ferrule 401 with the first optical fiber 402 inside.

As seen, both first and second walls of the container 408 have been perforated by the first ferrule 401 in the connected state. Especially, these walls may be formed by thin elastic materials, that may serve to prevent the fluid 409 from leaking during the penetration of the first and second walls.

In the connected state, at least a film of the sterilization fluid on the end of the first optical fiber 402 acts as a combined optical element between the first and second optical fibers 402, 404, i.e. it serves as optical connection, and it acts as a sterility barrier between the first and second optical fibers 402, 404. When entering the connected state, the sterilization fluid 409 has acted to sterilize at least the end of the first optical fiber 402.

Inside the cartridge 408, there may be a sponge (not visible) soaked in cleaning and sterilizing fluids 409 such as ethanol, or an iodine solution. The sponge may have a prefabricated puncture or hole or channel so that the non-sterile ferrule 401 can easily pass to the other side of the cartridge 408, despite that the hole may be squeezed tight. The latter is beneficial because a direct path between the two sides of the cartridge 408 (the sterile and non-sterile zone) is closed. It is also beneficial because the non-sterile ferrule 401 and fiber 402 is rubbed by the sponge when inserted and hence a mechanical cleaning of the ferrule 401 and fiber 402 is achieved.

Figure 5:
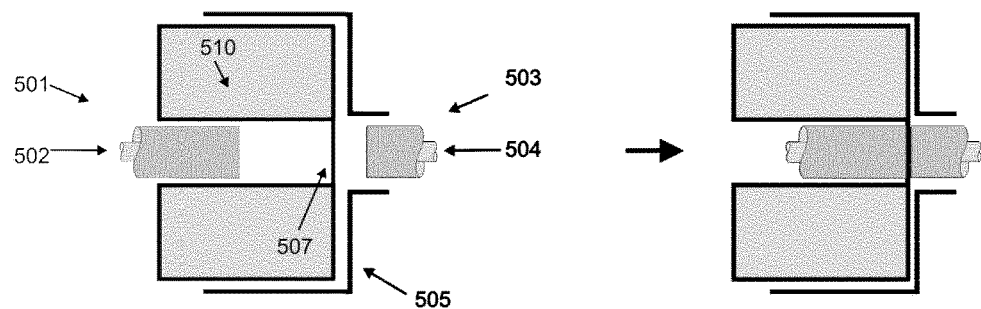
FIG. 5 shows a sketch of an embodiment with a sterile plug and membrane.

FIG. 5 shows side view sketches of an embodiment for connecting first and second ferrules 501, 503, with respective optical fibers 502, 504 arranged inside. Again, the sketch to the left shows a disconnected state, while the connected state is shown to the right. This embodiment comprises a plug 510 with a hole through which the sterile optical fiber and ferrule 501, 502 can be inserted from one end. At the opposite end of the plug 510, a thin transparent membrane 507 is present, similar to the one in the embodiment of FIG. 2. The plug 510 is shaped to fit into a receiving body 505 into which the second ferrule 503 fits from the opposite side.

This embodiment is advantageous, since not only the membrane 507 creates a sterility barrier, but also the plug 510 serves to shield the sterile optical fiber 502 from the receiving body 505. Therefore, the receiving body 505 does not have to be sterile, hereby potentially saving costs. Potentially, a sterile sleeve could be attached to the plug 510 and be draped over the receiving body 505 to shield the whole receiving body 505 from the sterile zone.

Figure 6:
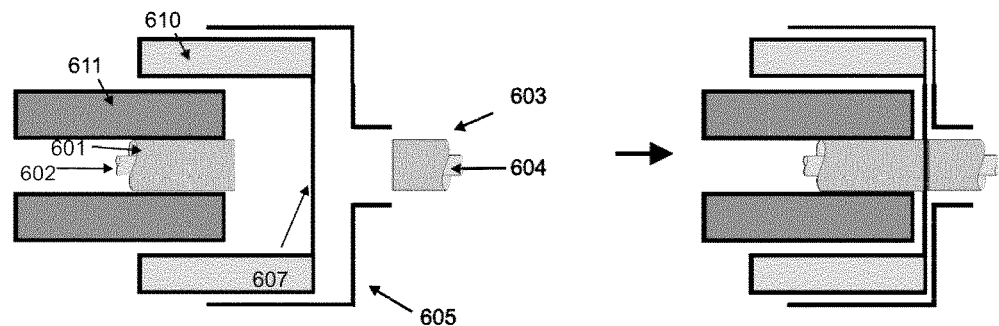
FIG. 6 shows a sketch of an embodiment similar to FIG. 5, but with an additional plug.

FIG. 6 shows side view sketches of yet another embodiment for connecting first and second ferrules 601, 603, with respective optical fibers 602, 604 arranged inside. Again, the sketch to the left shows a disconnected state, while the connected state is shown to the right. This can be seen as a further refinement on the embodiment of FIG. 5, in that this embodiment comprises a plug 610 with a hole through which the sterile optical fiber and ferrule 601, 602 can be inserted from one end. At the opposite end of the plug 610, a thin transparent membrane 607 is present, similar to the one in the embodiment of FIG. 2. The plug 610 is shaped to fit into a receiving body 605 into which the second ferrule 603 fits from the opposite side.

However, in this embodiment the hole in the plug 610 is larger, and a secondary plug 611 serves to receive the sterile optical fiber and ferrule 601, 602 can be inserted from one end of a through-going hole in the middle. The advantage of having a plug 611 in a plug 610 is that the outside plug 610 can be inserted at the beginning and be kept there during the whole procedure. The secondary plug 611 can be inserted and removed from the primary plug 610 without leaving the sterile zone. This arrangement allows easy loading of several different sterile optical fibers sequentially in the same interconnect. Furthermore, it is possible to have fluid inserts and outlets in the primary plug 610 to flush and clean the sterile optical fiber 602.

In general, possible materials for the optical element in the various embodiments described are: fluorinated polymers, polyethylene, and latex. For the embodiment with an optically transparent membrane, it may be preferred to use a material with a refractive index of 1.2 to 1.6, e.g. 1.4 to 1.5, e.g. 1.44-1.48, such as close to 1.46, which is the typical refractive index of the cores in optical fibers. Preferably, the material should be thin, strong, and transparent in the relevant wavelength range. For example the near infrared wavelength range, more specifically in the wavelength range of 1530-1565 nm.

The optical connector according to the invention is applicable within many applications, especially where a miniature and reversible connection for sterile environment is desirable. Especially, the application entails minimally invasive medical interventions, and the use of instruments that have a (optical) transmission line or cable running outside a sterile zone.

Figure 7:
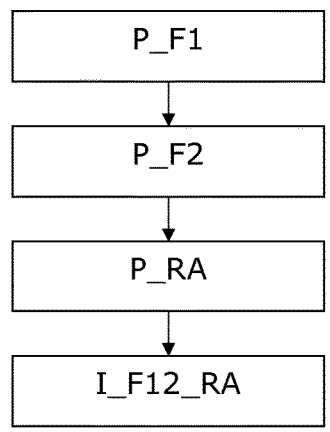
FIG. 7 illustrates a diagram of steps of a method embodiment.

FIG. 7 illustrates steps of a specific method embodiment for reversibly connecting a first and a second optical fiber. The method embodiment comprises providing P_F1 a first ferrule with a first optical fiber arranged inside, and providing P_F2 a second ferrule with a second optical fiber arranged inside. Next step is to provide P_RA a receptacle arrangement with an optical element, and finally inserting I_F12_RA end parts of both of the first and second ferrules into the receptacle arrangement such that an optical connection is provided between the first and second optical fibers via the optical element, wherein the optical element serves as a sterility barrier between the first and second optical fibers.

To sum up, the invention provides an optical connector system for reversible optical connection between two optical fibers 102, 104 with their end parts inside respective ferrules. A receptacle arrangement has a receiving body 105 for receiving at least one of the ferrules 103. An optical element 106 of the receptacle arrangement serves to provide optical connection between the two optical fibers in a connected state of the optical connector system, and at the same time, the optical element 106 serves as a sterility barrier between the two optical fibers. The optical element 106 can be an optical waveguide, e.g. a piece of optical fiber similar to the two optical fibers 102, 104, and arranged within the receiving body 105. Alternatively, the optical element may be a thin flexible membrane 207, 307 which is optically transparent. As a further alternative, the optical element may be a sterilizing fluid 409 arranged in side a container that can be punctured upon insertion of one of the ferrules 401, 403 into the container 408, to allow an optical fiber end to be sterilized by the fluid 409 prior to entering into the connected state. In a further embodiment, an optical lens 312 is used to project light from one fiber end through a membrane 307 to the opposite fiber end.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

The invention claimed is:
1. A medical optical system, comprising:
an optical connector system arranged to provide a reversible optical connection between associated first and second optical fibers, each comprising multiple fiber cores, the optical connector system comprising:
a first ferrule with an outer body and arranged for having an end portion of the associated first optical fiber) arranged inside,
a second ferrule with an outer body and arranged for having an end portion of the associated second optical fiber arranged inside,
a receptacle arrangement comprising a receiving body, wherein the receptacle arrangement is arranged to receive an end part of the outer body of at least the second ferrule, wherein the receptacle arrangement further comprises an optical element serving to provide an optical connection between the associated first and second optical fibers in a connected state of the optical connector system, and wherein the optical element serves as a sterility barrier between the associated first and second optical fibers, the optical connector system being configured for rotational alignment of the first and second optical fibers in the connected state of the connector system wherein the optical element provides connection between each single fiber core of the first and second optical fibers, and
a rotational locking arrangement preventing relative rotation between the first and second ferrules.

2. Medical optical system according to claim 1, wherein the receptacle arrangement is arranged to receive the end part of the outer body of the first ferrule in one end, and to receive an end part of the outer body of the second ferrule in its opposite end, and wherein the optical element comprises an optical waveguide arranged within the receiving body.

3. Medical optical system according to claim 1, wherein the optical element comprises an optically transparent membrane.

4. Medical optical system according to claim 3, wherein the optically transparent membrane is flexible, and arranged to partially encapsulate the associated first or second optical fiber in the connected state.

5. Medical optical system according claim 3, comprising a plug arranged to receive the first ferrule, and wherein the plug is arranged to fit inside the receiving body.

6. Medical optical system according to claim 3, comprising a first plug arranged to fit inside the receiving body, and a second plug arranged to receive the first ferrule and to fit inside the first plug.

7. Medical optical system according to claim 3, comprising a second optical element arranged to project light from one of the associated first and second optical fibers via the optically transparent membrane to the opposite one of the associated first and second optical fiber.

8. Medical optical system according to claim 1, wherein the receptacle arrangement comprises a container with a sterilizing fluid.

9. Medical optical system according to claim 8, wherein said container is arranged to receive the first ferrule and to puncture upon insertion of the first ferrule into the container, so as to allow sterilization of at least an end part of the associated first optical fiber by means of contact with the sterilizing fluid, upon insertion of the first ferrule into the container.

10. Medical optical system according to claim 8, comprising a sponge element within the container, wherein at least a part of said sterilizing fluid is soaked into the sponge element, and wherein the sponge element is arranged to mechanically clean at least part of the associated first optical fiber during insertion of the first ferrule into the container.

11. Medical optical system according to claim 10, wherein the sponge element has a prefabricated hole arranged for the first ferrule to penetrate through, so as to allow the associated first optical fiber to provide optical connection with the associated second optical fiber, in the connected state.

12. Medical optical system according to claim 1, wherein the receiving body is arranged to surround end parts of outer bodies of both of the first and second ferrules in a connected state of the optical connector system.

13. Medical system comprising an interventional medical device optically connected to an optical system, wherein the optical system comprises:
    first and second optical fibers, each comprising multiple fiber cores, and
    an optical connector system arranged to provide a reversible optical connection between said first and second optical fibers, the optical connector system comprising:
    a first ferrule with an outer body and an end portion of the first optical fiber arranged inside,
    a second ferrule with an outer body and an end portion of the second optical fiber arranged inside,
    a receptacle arrangement comprising a receiving body, wherein the receptacle arrangement is arranged to receive an end part of the outer body of at least the second ferrule, wherein the receptacle arrangement further comprises an optical element serving to provide optical connection between the associated first and second optical fibers in a connected state of the optical connector system, and wherein the optical element serves as a sterility barrier between the associated first and second optical fibers, the optical connector system being configured for rotational alignment of the first and second optical fibers in the connected state of the connector system wherein the optical element provides connection between each single fiber core of the first and second optical fibers, and
    a rotational locking arrangement preventing relative rotation between the first and second ferrules.

14. A method for reversibly connecting first and second optical fibers, each comprising multiple fiber cores of a medical optical system, the method comprising:
    providing (P_F1) a first ferrule with an outer body and an end portion of the first optical fiber arranged inside,
    providing (P_F2) a second ferrule with an outer body and an end portion of the second optical fiber arranged inside, and
    providing (P_RA) a receptacle arrangement comprising an optical element,
    inserting (I_F12_RA) at least and end part of the outer body of the first ferrule into the receptacle arrangement, so at to provide optical connection between the first and second optical fibers via the optical element, wherein the optical element provides connection between each single fiber core of the first and second optical fibers wherein the optical element serves as a sterility barrier between the first and second optical fibers, and wherein the optical connector system is configured for rotational alignment of the first and second optical fibers in the connected state of the connector system, and
    providing a rotational locking arrangement preventing relative rotation between the first and second ferrules.

\* \* \* \* \*